United States Patent
Wietelmann et al.

(10) Patent No.: US 9,509,014 B2
(45) Date of Patent: Nov. 29, 2016

(54) GALVANIC CELL HAVING A LITHIUM METAL OR AN ALLOY COMPRISING A LITHIUM METAL AS ANODE MATERIAL AND AN ELECTROLYTE HAVING LITHIUM ... COMPLEX SALT

(75) Inventors: Ulrich Wietelmann, Friedrichsdorf (DE); Thorsten Buhrmester, Darmstadt (DE); Ute Emmel, Frankfurt am Main (DE); Rebecca Metzger, Eppstein (DE)

(73) Assignee: Chemetall GmbH (DE)

( * ) Notice: Subject to any disclaimer, the term of this patent is extended or adjusted under 35 U.S.C. 154(b) by 635 days.

(21) Appl. No.: 13/201,640
(22) PCT Filed: Feb. 17, 2010
(86) PCT No.: PCT/EP2010/000992
§ 371 (c)(1),
(2), (4) Date: Dec. 19, 2011
(87) PCT Pub. No.: WO2010/094467
PCT Pub. Date: Aug. 26, 2010

(65) Prior Publication Data
US 2012/0082900 A1    Apr. 5, 2012

(30) Foreign Application Priority Data
Feb. 18, 2009 (DE) .................. 10 2009 000 977

(51) Int. Cl.
| | |
|---|---|
| H01M 4/38 | (2006.01) |
| H01M 10/056 | (2010.01) |
| H01M 10/0567 | (2010.01) |
| H01M 10/0568 | (2010.01) |
| H01M 10/0569 | (2010.01) |
| H01M 10/052 | (2010.01) |
| H01M 10/42 | (2006.01) |
| C07F 9/6574 | (2006.01) |
| C07F 5/02 | (2006.01) |
| C07F 5/04 | (2006.01) |
| H01M 4/134 | (2010.01) |

(52) U.S. Cl.
CPC ............ *H01M 10/052* (2013.01); *C07F 5/022* (2013.01); *C07F 5/04* (2013.01); *C07F 9/65748* (2013.01); *H01M 4/382* (2013.01); *H01M 10/0567* (2013.01); *H01M 10/0568* (2013.01); *H01M 10/4235* (2013.01); *H01M 4/134* (2013.01); *Y02E 60/122* (2013.01)

(58) Field of Classification Search
USPC ......................................... 429/188
See application file for complete search history.

(56) References Cited

U.S. PATENT DOCUMENTS

| | | | |
|---|---|---|---|
| 6,693,212 B1 | 2/2004 | Wietelmann et al. | |
| 2005/0095503 A1* | 5/2005 | Adachi et al. ................ | 429/188 |
| 2006/0240327 A1* | 10/2006 | Xu ..................... | H01M 10/0525 429/324 |
| 2006/0269844 A1* | 11/2006 | Deng et al. ................... | 429/325 |
| 2006/0269846 A1* | 11/2006 | Xu et al. ...................... | 429/326 |

(Continued)

FOREIGN PATENT DOCUMENTS

| | | |
|---|---|---|
| DE | 199 33 898 A1 | 2/2001 |
| DE | 10 2004 011522 A1 | 9/2004 |

(Continued)

*Primary Examiner* — Daniel Gatewood
(74) *Attorney, Agent, or Firm* — Jeremy J. Kliebert

(57) ABSTRACT

A galvanic cell having a lithium metal or an alloy comprising a lithium metal as anode material, having an electrolyte comprising lithium bis(oxalate)borate and at least one other lithium complex salt in an aprotic solvent or solvent mixture, in the ratio of lithium complex salt in the conducting salt equals 0.01 to 20 mol %.

16 Claims, 5 Drawing Sheets

(56) References Cited

U.S. PATENT DOCUMENTS

2007/0269715 A1* 11/2007 Panitz et al. ............. 429/188
2010/0143806 A1   6/2010 Dietz et al.

FOREIGN PATENT DOCUMENTS

DE   102008040153 A1   1/2009
EP   1 487 047 A2   12/2004

* cited by examiner

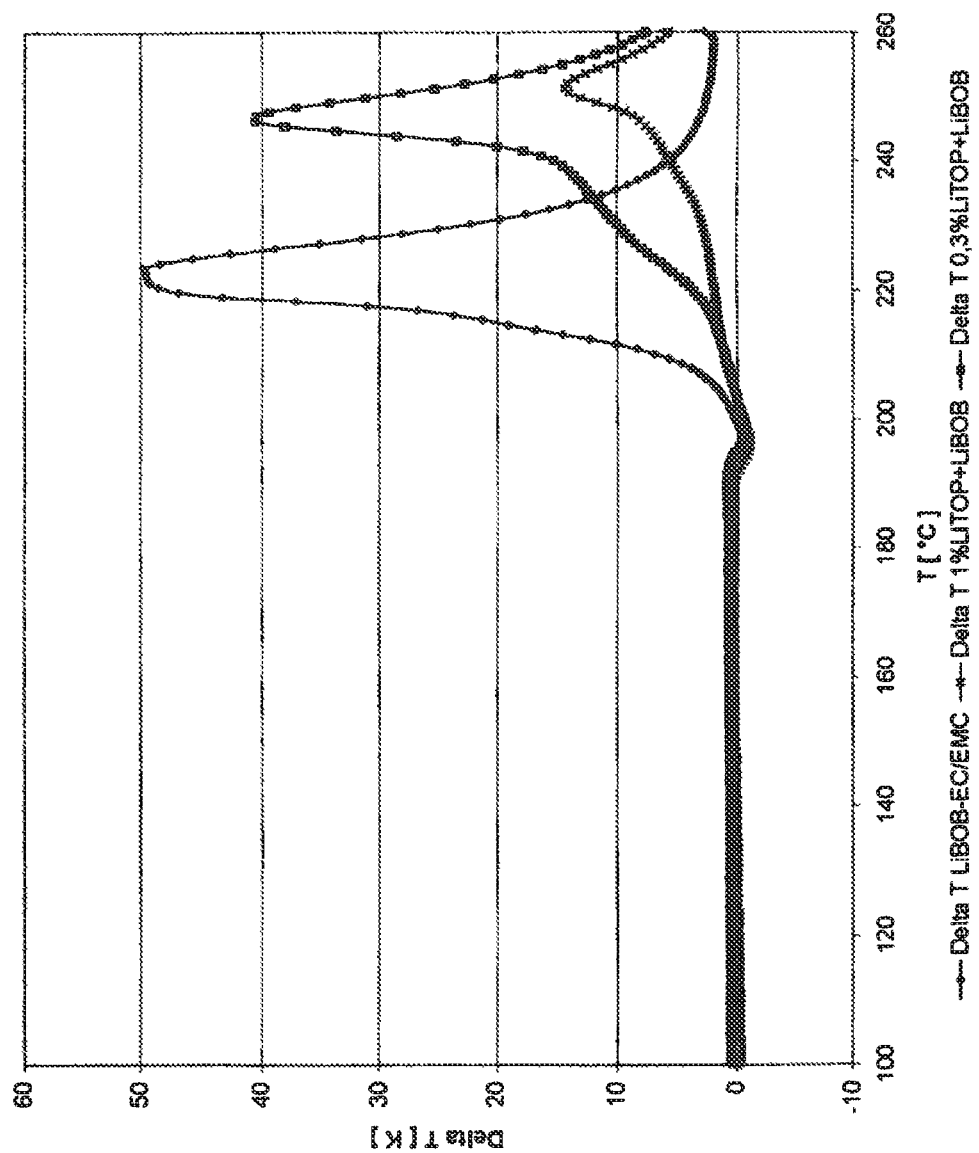

GALVANIC CELL HAVING A LITHIUM METAL OR AN ALLOY COMPRISING A LITHIUM METAL AS ANODE MATERIAL AND AN ELECTROLYTE HAVING LITHIUM . . . COMPLEX SALT

RELATED APPLICATIONS

This application is a §371 application of PCT/EP2010/000992 filed Feb. 17, 2010, and claims priority from German Patent Application No. 10 2009 000 977.9 filed Feb. 18, 2009.

The invention relates to a galvanic cell having a lithium metal or an alloy containing a lithium metal as anode material.

Mobile electronic devices require ever more powerful rechargeable batteries for an independent power supply. In addition to nickel/cadmium and nickel/metal hydride rechargeable batteries, lithium batteries in particular, which in comparison to the first-named systems have a markedly higher energy density, are suitable for these purposes. Large-format lithium rechargeable batteries are also to be used in future for e.g., static applications (power back-up) and in the automotive sector for traction purposes (hybrid drives or electric-only drives). Lithium-ion batteries, in which a graphite-containing substance is used as the anode, are currently being developed and used for this purpose. In the charged state graphite anodes can generally store (intercalate) no more than 1 lithium per 6 carbon atoms, corresponding to a limiting stoichiometry $LiC_6$. This results in a lithium density of max. 8.8 wt. %. The anode material thus brings about an undesired restriction of the energy density of such battery systems.

Instead of lithium intercalation anodes such as graphite, lithium metal or an alloy containing a lithium metal (e.g. alloys of lithium with aluminium, silicon, tin, titanium or antimony) can in principle also be used as the anode material. In comparison to the commonly used graphite intercalation cathode, this principle would allow a markedly higher specific lithium charge and hence energy density. Unfortunately such lithium-metal-containing systems exhibit unfavourable safety characteristics. In unfavourable operating conditions (e.g. elevated temperatures), decomposition reactions can occur which lead to a dangerous run-away situation. The battery then begins a spontaneous heating process, which can result in an explosive formation of gas and destruction of the battery casing. Owing to the combustibility of common electrolyte solutions consisting of organic solvents or mixtures thereof such as carbonic acid esters, for example ethylene carbonate (EC), propylene carbonate (PC), ethyl methyl carbonate (EMC), lactones, for example γ-butyrolactone (γ-BL), or ethers, for example dimethoxyethane (DME), fires can occur. As current lithium batteries contain an unstable, fluorine-containing supporting electrolyte ($LiPF_6$ or $LiBF_4$), dangerous, caustic and toxic decomposition products (hydrogen fluoride and volatile fluorine-containing organic products) also form during such events. For these reasons, rechargeable batteries containing lithium metal have hitherto been produced only at a micro-design scale, for example button cells.

The object of the invention is to overcome the disadvantages of the prior art as described above and to propose a safe, rechargeable battery system with an energy density exceeding that of lithium-ion technology.

According to the invention the object is achieved by means of a galvanic cell having a lithium metal or an alloy containing a lithium metal as anode material, said galvanic cell having an electrolyte containing lithium bis(oxalato)borate and at least one further lithium complex salt of formulae I and/or II in an aprotic solvent or solvent blend, wherein

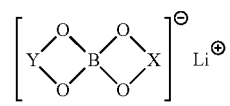

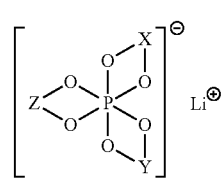

wherein the proportion of compound (I) and/or (II) in the supporting electrolyte is 0.01 to 20 mol % and X, Y and Z in the formulae (I, II) is a bridge which is connected to the boron or phosphorus atom by two oxygen atoms and is selected from

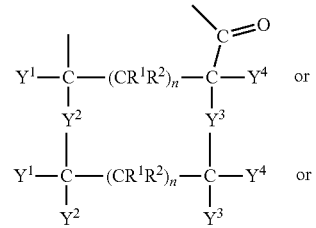

$n = 0, 1$

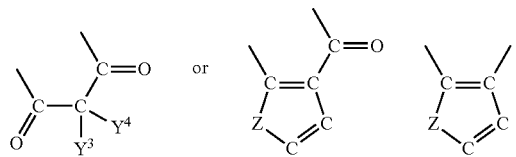

where
$Z=N$, $N=C$;
$S$, $S=C$;
$O$, $O=C$;
$C=C$ $Y^1$ and $Y^2$ together denote O, m=1, n=0 and $Y^3$ and $Y^4$ are independently of each other H or an alkyl radical having 1 to 5 C atoms, or $Y^1$, $Y^2$, $Y^3$, $Y^4$ are each independently of one another OR (where R=alkyl radical having 1 to 5 C atoms), H or an alkyl radical $R^1$, $R^2$ having 1 to 5 C atoms, and where m, n=0 or 1.

Surprisingly it has been found that when mixed with one of the cited complex additives, LiBOB appears to form a thin, extremely thermally stable layer on the lithium metal or lithium metal alloy surface, which effectively prevents a decomposition reaction between the lithium-metal-containing anode material and the electrolyte component. Furthermore, the undesired gas formation at elevated temperatures, which can cause a battery cell to explode, is substantially reduced. This effect is not observed if an electrolyte containing exclusively LiBOB as supporting electrolyte or containing a fluorine-containing supporting electrolyte is used.

The galvanic cell advantageously contains only one of the compounds according to formula I and/or II in an amount from 0.1 to 10 wt. %.

Alternatively the galvanic cell contains only one of the compounds according to formula I and/or II in an amount from 0.2 to 5 wt. %.

A galvanic cell in which only fluorine-free materials are contained in the electrolyte is particularly preferred.

A galvanic cell containing lithium tris(oxalato)phosphate or lithium maionato-oxalatoborate as lithium complex salts is most particularly preferred.

A galvanic cell in which the electrolyte is present as a liquid or gel electrolyte is also preferred.

The solvent in the electrolyte of the galvanic cell is preferably propylene carbonate or a mixture of ethylene carbonate and ethyl methyl carbonate.

According to the invention the galvanic cell is used to produce large-format batteries for electric drives or for static applications.

The invention is illustrated in more detail below by reference to five examples, three comparative examples and five figures.

To demonstrate the surprising observations mentioned above, experiments with lithium metal/electrolyte mixtures are described in the following section. Anhydrous mixtures of lithium metal (battery grade, i.e. with a sodium content below 200 ppm), lithium supporting electrolytes ($LiPF_6$ or LiBOB) and optionally a further lithium complex salt, e.g. lithium tris(oxalato)phosphate (LiTOP) or lithium malonato-oxalatoborate (LiMOB), were produced in conventionally used solvents (PC or EC-EMC) and approximately 2.5 g of such mixtures were introduced into steel autoclaves with an approximate capacity of 3 ml in an argon-filled glove box. These vessels were heated in a RADEX apparatus and the thermal effects that occurred were measured (DSC). In further tests the steel autoclaves were connected to pressure sensors to allow gas formation to be observed as well.

FIG. 5 shows DSC tests of LiBOB-containing, fluorine-free solutions in EC-EMC (50:50) in the presence of lithium metal granules.

FIG. 1 shows the behaviour of fluorine-free, LiBOB-based electrolyte solutions in the presence of Li metal (Examples 1 to 3 and comparative example 1.)

Figure 1:
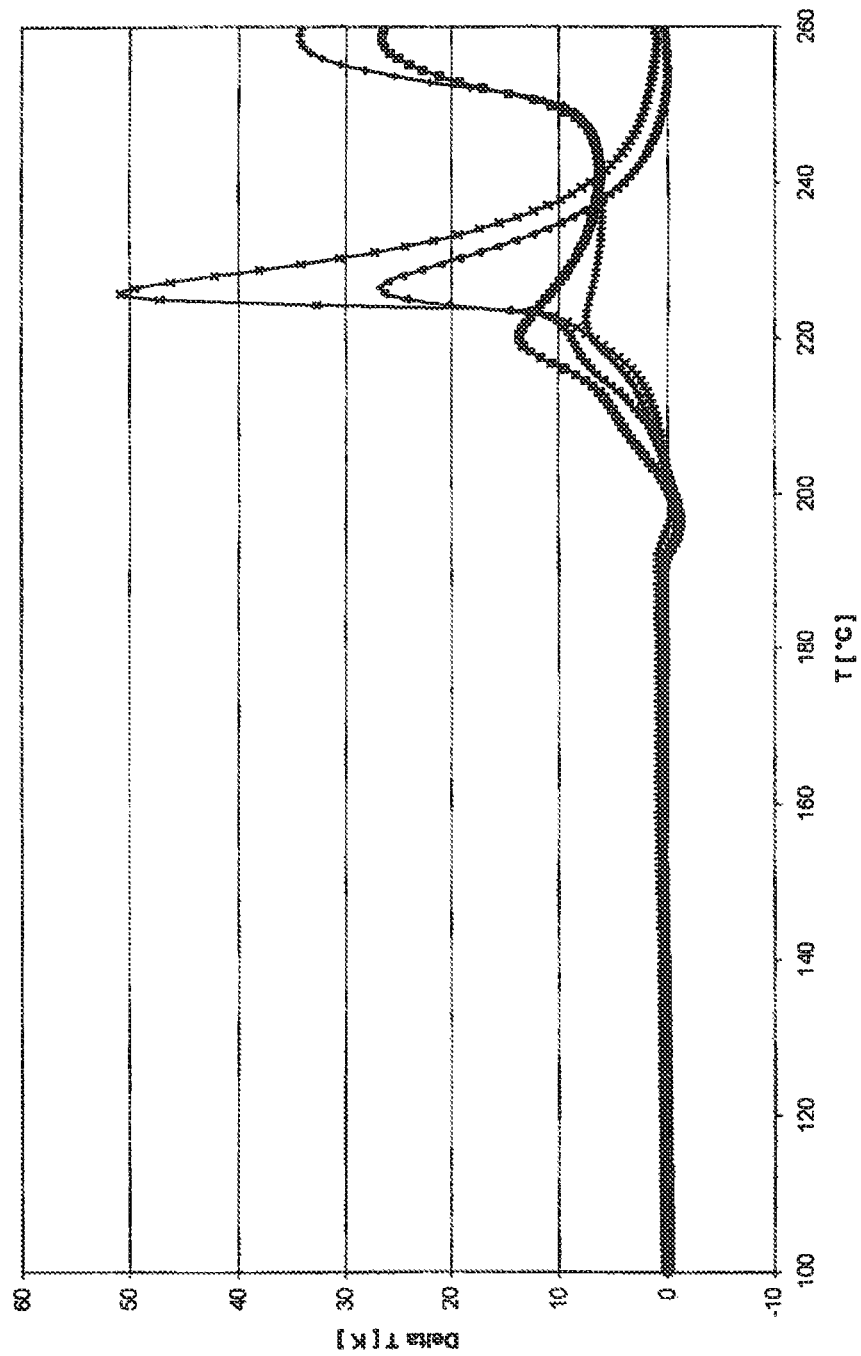
FIG. 1 shows the behaviour of fluorine-free, LiBOB-based electrolyte solutions in the presence of Li metal.
Figure 2:
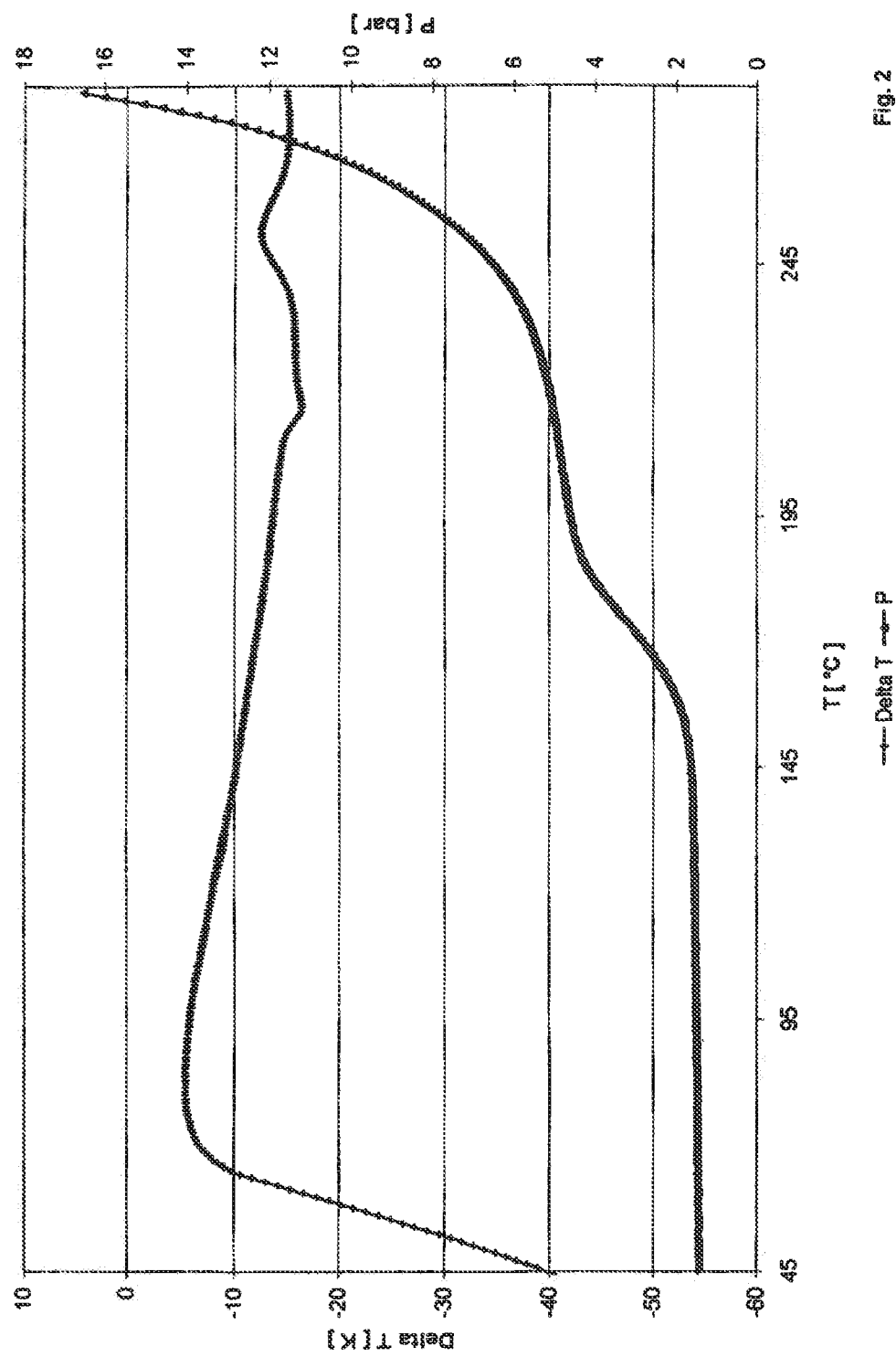
FIG. 2 shows the DSC test and simultaneous pressure monitoring of a PC solution containing 14% LiBOB and 1% LiTOP in the presence of lithium metal granules.
Figure 3:
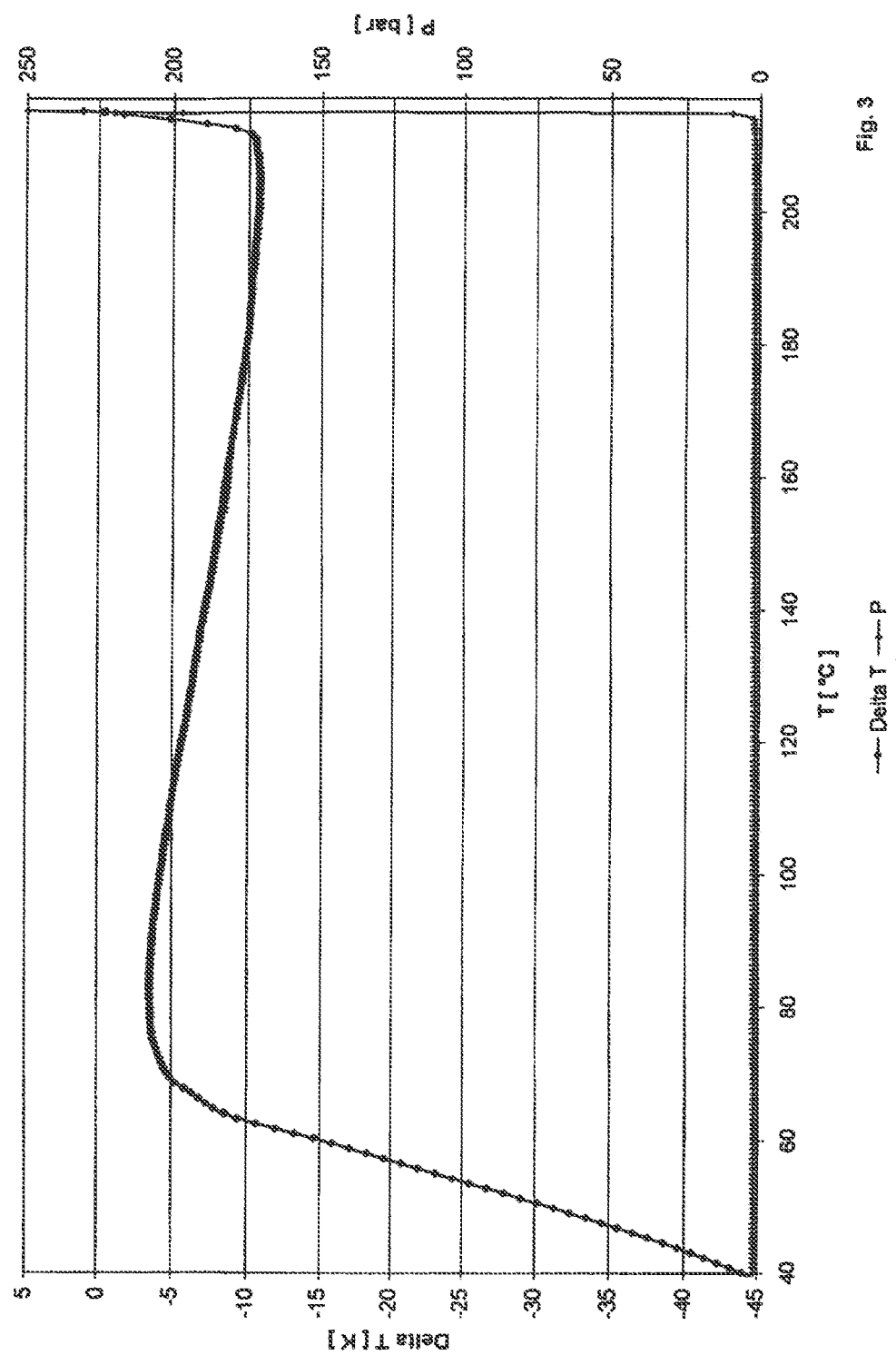
FIG. 3 shows the DSC test and simultaneous pressure monitoring of a solution of 15% $LiPF_6$ in PC in the presence of lithium metal granules.
Figure 4:
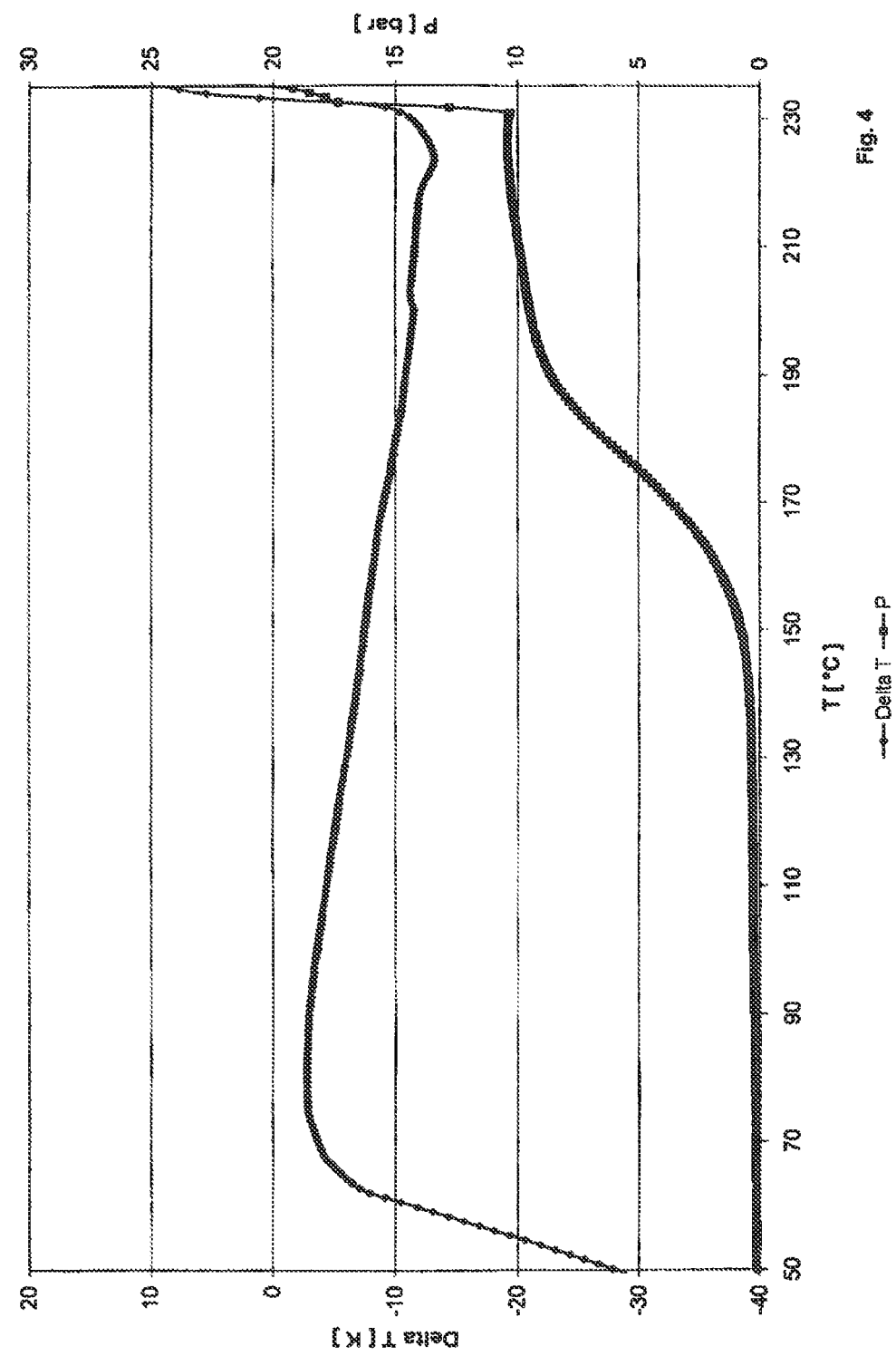
FIG. 4 shows the DSC test and simultaneous pressure monitoring of a PC solution containing 14% $LiPF_6$ and 1% LiTOP in the presence of lithium metal granules.

In all experiments a weak endotherm is detected at an oven temperature of approx. 190-200° C., which can be attributed to the melting of the lithium metal content.

In comparative example 1 (not according to the invention) exclusively 15 wt. % of LiBOB-containing electrolyte is used as the supporting electrolyte. A strongly exothermic event can be seen (red curve) with a peak temperature of approx. 205° C. If by contrast a PC solution containing 14 wt. % LiBOB and 1 wt. % LiMOB is used as described in Example 1 (light blue curve), a markedly reduced evolution of heat is observed. This effect is even more evident with the partial substitution for LiBOB of 0.3% (Example 2—green curve) or 1% (Example 3—dark blue curve) LiTOP.

In Example 3 according to the invention, simultaneous pressure measurement shows that the scarcely exothermic decomposition reaction (peak oven temperature approx. 250° C.) of a LiBOB-LiTOP electrolyte is accompanied by only a very slight evolution of gas.

Comparative example 2 below shows the pressure-temperature behaviour of an electrolyte solution based purely on $LiPF_6$. If an oven temperature of approx. 210° C. is exceeded, a highly exothermic decomposition event begins, accompanied by an explosive formation of gas. The pressure (blue curve) rises in a matter of seconds from <10 bar to >250 bar.

Examples 4 and 5 below (electrolyte solutions of LiBOB/LiTOP) show in comparison to the example not according to the invention (electrolyte solution containing only LiBOB) that the desired lithium metal stabilisation also takes place in the EC-EMC solvent blend. The addition of LiTOP shifts the peak temperature of the decomposition upwards by approximately 30° C., and the release of heat is very markedly reduced, in other words the undesired decomposition reaction between the components lithium metal and organic electrolyte solution takes place to a lesser extent in the examples according to the invention.

The invention claimed is:

1. A galvanic cell comprising an anode material and an electrolyte in a solvent;
    wherein the anode material comprises a lithium metal or an alloy containing a lithium metal;
    wherein said electrolyte consists essentially of lithium bis(oxalato)borate and at least one further lithium complex salt selected from the group consisting of lithium tris(oxalato)phosphate and lithium malonato-oxalatoborate;
    wherein said further lithium complex salt is present in an amount of from 0.2 to 10 wt. %.

2. A galvanic cell according to claim 1, wherein said further lithium complex salt is present in an amount of from 0.2 to 5 wt. %.

3. A galvanic cell according to claim 1, wherein said further lithium complex salt is lithium malonato-oxalatoborate.

4. A galvanic cell according to claim 1, wherein said electrolyte is a liquid or a gel.

5. A galvanic cell according to claim 1, wherein said solvent is propylene carbonate or a mixture of ethylene carbonate and ethyl methyl carbonate.

6. A large format battery for electric drives or for static applications comprising said galvanic cell according to claim 1.

7. A galvanic cell according to claim 1, wherein said further lithium complex salt is lithium tris(oxalato)phosphate.

8. A galvanic cell according to claim 7, wherein said electrolyte is a liquid or a gel.

9. A large format battery for electric drives or for static applications comprising said galvanic cell according to claim 7.

10. A large format battery for electric drives or for static applications comprising said galvanic cell according to claim 2.

11. A large format battery for electric drives or for static applications comprising said galvanic cell according to claim 3.

12. A galvanic cell according to claim 1, wherein said electrolyte is a gel.

13. A galvanic cell having a lithium metal or an alloy containing a lithium metal as anode material and an electrolyte in a solvent;
   wherein said electrolyte consists of lithium bis(oxalato)borate and at least one further lithium complex salt selected from the group consisting of lithium tris(oxalato)phosphate and lithium malonato-oxalatoborate;
   wherein said further lithium complex salt is present in an amount of from 0.2 to 10 wt. %.

14. A galvanic cell according to claim 13 wherein said solvent is propylene carbonate or a mixture of ethylene carbonate and ethyl methyl carbonate.

15. A galvanic cell according to claim 13, wherein said further lithium complex salt is lithium tris(oxalato)phosphate.

16. A galvanic cell according to claim 13, wherein said further lithium complex salt is lithium malonato-oxalatoborate.

* * * * *